United States Patent [19]

Holtkamp

[11] Plant 4,352

[45] Dec. 19, 1978

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "Optimara", Isselburg, Fed. Rep. of Germany

[21] Appl. No.: 880,328

[22] Filed: Feb. 22, 1978

[51] Int. Cl.[2] ..... A01H 5/00

[52] U.S. Cl. ..... Plt./69

[58] Field of Search ..... Plt./69

*Primary Examiner*—Robert E. Bagwill
*Attorney, Agent, or Firm*—Beall & Jeffery

[57] ABSTRACT

An African violet named Kentucky having strong and upright stems each carrying up to 10 flowers which are non-dropping blue-violet in color, durable and of typical violet shape. The new cultivar has dark green leaves, and sturdy growth habit.

1 Drawing Figure

1

The present invention comprises a new and distinct cultivar of African violet plant, botanically known as *Saintpaulia ionantha,* and hereinafter referred to by the cultivar name Kentucky. The new cultivar, identified during the breeding and selection process by the numbers 22/15, 18/77 is a product of a planned breeding program. Kentucky is characterized principally by its regular violet-shaped flowers, which do not drop, dark-green leaves, sturdy growth, and strong and straight stems. The flower color is purple.

The new cultivar was originated from a cross made in a controlled breeding program in Isselburg, Rhineland, Germany. The female, or seed parent is unpatented and identified as XIX 4194 blue (RHS 89 A). The male, or pollen parent is also unpatented and identified as 4179 blue-violet.

Kentucky was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Kentucky, which in combination distinguish this African violet as a new and distinct cultivar:

1. Very strong and upright flower stems.
2. Each flower stem carries 8–10 single flowers.
3. When blooming for the first time, there are 7–9 flower stems.
4. The flowers are blue-violet in color and do not drop, that is, the flowers at maturity dry on the stem rather than dropping off the stem.
5. Dark-green leaves.
6. Single, violet-shaped flowers.

The accompanying photographic drawing shows a typical specimen plant of the new cultivar. The colors appearing in the photograph are as true as possible with color illustrations of this type.

2

In the following description, color references are made to the Royal Horticultural Society color chart (RHS), 1966 edition, except where general color terms of ordinary significance are obvious.

Botanical classification: *Saintpaulia ionantha,* Ramat. cv. Kentucky.

Parentage:

*Male parent.*—XIX 4179 blue-violet.

*Female parent.*—XIX 4194 blue.

Propagation: The new cultivar holds its distinguishing characteristics through successive propagations by leaf cuttings and by division of shoots.

Plant: From 9 cm. to 10 cm. tall when grown in pots, and approximately 25 cm. in diameter when fully grown.

Leaves:

*General form.*—Oblong to round.

*Diameter.*—50–60 mm.

*Texture.*—Slightly round and hairy.

*Veins.*—Well pronounced, light-green.

*Color (upperside).*—131 A, dark green.

*Color (underside).*—Young leaves: 145 C, old leaves 70 A.

*Petiole.*—Brown-red.

Flowers:

*Buds.*—Round shape, diameter 6–7 mm. before opening, 83 A.

*Sepals.*—Five, spear-shaped, 5–6 mm. long. Color: reddish-brown, green secondary hue, 183 A. Calyx: with receptacle and seed vessel joined. Aspect: funnel-shaped. Peduncle: straight, 20–25 mm. long.

Individual flowers:

*Size.*—Up to 40 mm. in total flower diameter, the large petals being 22 mm. long and 17 mm. wide, and the small petals being 17 mm. long and 13 mm. wide.

*Color.*—Upperside: between 89 B and 89 C. Underside: 88 B.

*Borne.*—Most flower stems carry up to nine single flowers.

*Shape.*—Five Petals, two small and three large.

*Arrangement.*—Flowers carried on strong and upright flower stems, with up to nine or more flowers on each stem.

*Flowering time.*—The first flowers show 8–10 weeks after potting; after 9–11 weeks, the plant is in full bloom.

Reproductive organs:

*Stamens.*—Two in number.

*Anthers.*—Four anthers, 7 B.

*Arrangement.*—The stamens are underneath the seed vessel and are joined to the receptacle by two short stems.

*Filaments.*—3–5 mm. long.

*Styles.*—7–8 mm. long, color 89 A.

*Pollen color.*—7 C.

Roots: Root system is well developed; the tips of the young roots are white, turning brownish as plant matures.

Disease resistance: No disease problems noticed to date.

General observations: Kentucky is a very sturdy plant with dark-green leaves which are slightly rough and hairy on the upperside. The flowers are non-dropping, intensive blue-violet in color and regular in shape. The flowers are very durable and are carried on strong stems each of which carries up to 10 single flowers.

I claim:

1. A new and distinct cultivar of African violet known by the cultivar name Kentucky and having the combined characteristics of strong and upright stems each carrying up to 10 flowers; non-dropping, blue-violet and durable flowers regular in shape; dark green leaves, and sturdy growth habit.

* * * * *

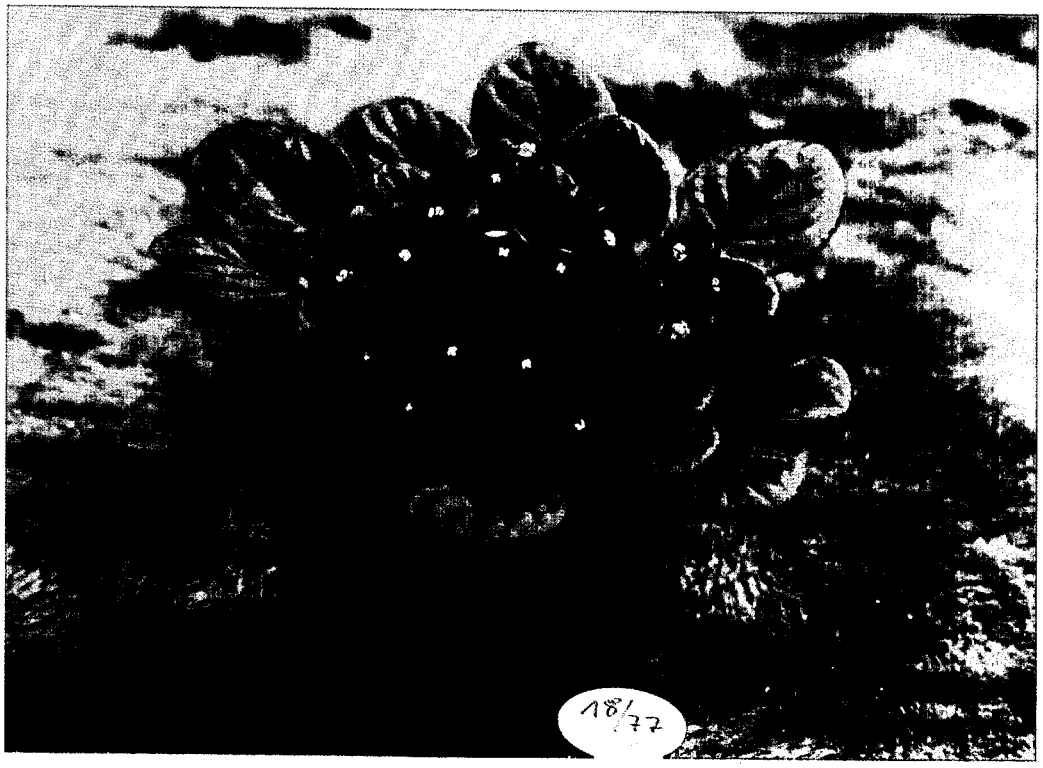
18/77